United States Patent
Li et al.

(10) Patent No.: US 10,716,542 B2
(45) Date of Patent: Jul. 21, 2020

(54) ULTRASOUND TRANSDUCER ASSEMBLY

(71) Applicant: FUJIFILM SonoSite, Inc., Bothell, WA (US)

(72) Inventors: Wei Li, Bothell, WA (US); Gregg Frey, Issaquah, WA (US); Simon Hsu, Mercer Island, WA (US)

(73) Assignee: FUJIFILM SONOSITE, INC., Bothell, WA (US)

( * ) Notice: Subject to any disclaimer, the term of this patent is extended or adjusted under 35 U.S.C. 154(b) by 745 days.

(21) Appl. No.: 15/256,029

(22) Filed: Sep. 2, 2016

(65) Prior Publication Data

US 2017/0065253 A1 Mar. 9, 2017

Related U.S. Application Data

(60) Provisional application No. 62/214,185, filed on Sep. 3, 2015.

(51) Int. Cl.
| | |
|---|---|
| *H01L 41/312* | (2013.01) |
| *H01L 41/338* | (2013.01) |
| *A61B 8/00* | (2006.01) |
| *H01L 41/09* | (2006.01) |
| *G01N 29/24* | (2006.01) |

(Continued)

(52) U.S. Cl.
CPC ............ *A61B 8/4494* (2013.01); *B06B 1/067* (2013.01); *B06B 1/0622* (2013.01); *B06B 1/0644* (2013.01); *G01N 29/2406* (2013.01); *G01N 29/2437* (2013.01); *H01L 41/0986* (2013.01); *H01L 41/312* (2013.01); *H01L 41/338* (2013.01); *A61B 8/4444* (2013.01); *G01N 2291/0231* (2013.01)

(58) Field of Classification Search
CPC ............................ H01L 41/312; A61B 8/4494
See application file for complete search history.

(56) References Cited

U.S. PATENT DOCUMENTS

| | | |
|---|---|---|
| 5,030,874 A | 7/1991 | Saito et al. |
| 5,142,187 A | 8/1992 | Saito et al. |

(Continued)

FOREIGN PATENT DOCUMENTS

| | | |
|---|---|---|
| EP | 0707898 A2 | 4/1996 |
| EP | 1755359 A1 | 2/2007 |

(Continued)

OTHER PUBLICATIONS

International Searching Authority, International Search Report and Written Opinion, PCT Patent Application PCT/US2016/050171, dated Dec. 22, 2016, 15 pages.

(Continued)

*Primary Examiner* — Thomas M Dougherty
*Assistant Examiner* — Karen B Addison
(74) *Attorney, Agent, or Firm* — Womble Bond Dickinson (US) LLP

(57) ABSTRACT

Ultrasound transducer assemblies and associated systems and method are disclosed herein. In one embodiment, an ultrasound transducer assembly includes at least one matching layer overlies a transducer layer. A plurality of kerfs extends at least into the matching layer. In some aspects, the kerfs are at least partially filled with a filler material that includes microballoons and/or microspheres.

13 Claims, 6 Drawing Sheets

(51) Int. Cl.
  *B06B 1/06*  (2006.01)
  *B60B 1/06*  (2006.01)

(56) References Cited

U.S. PATENT DOCUMENTS

| | | | | |
|---|---|---|---|---|
| 5,311,095 | A * | 5/1994 | Smith | B06B 1/064 |
| | | | | 310/334 |
| 6,359,375 | B1 * | 3/2002 | Guo | B06B 1/0622 |
| | | | | 310/334 |
| 9,219,220 | B2 * | 12/2015 | Ko | H01L 41/083 |
| 2005/0042424 | A1 | 2/2005 | Frey et al. | |
| 2006/0028099 | A1 | 2/2006 | Frey | |
| 2009/0093722 | A1 | 4/2009 | Takeuchi et al. | |
| 2013/0169818 | A1 * | 7/2013 | Ko | H01L 41/083 |
| | | | | 348/163 |
| 2013/0293066 | A1 | 11/2013 | Tsuzuki et al. | |

FOREIGN PATENT DOCUMENTS

| | | |
|---|---|---|
| JP | 59-025500 A | 2/1984 |
| JP | 61-039700 A | 2/1986 |

OTHER PUBLICATIONS

Supplementary European Search Report and Written Opinion received for EP Patent Application No. 16843099.9, dated Apr. 24, 2019, 10 pages.

\* cited by examiner

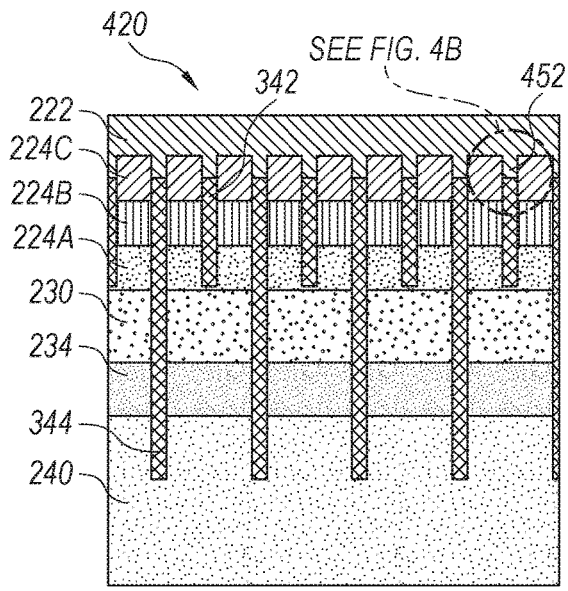
Fig. 4A
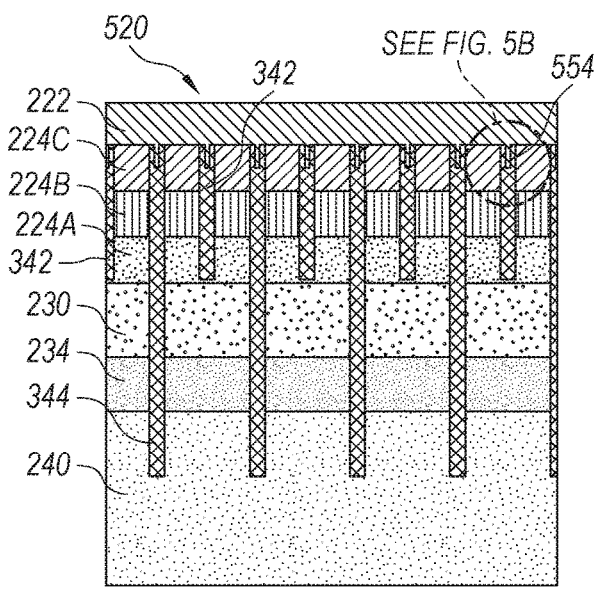
Fig. 5A
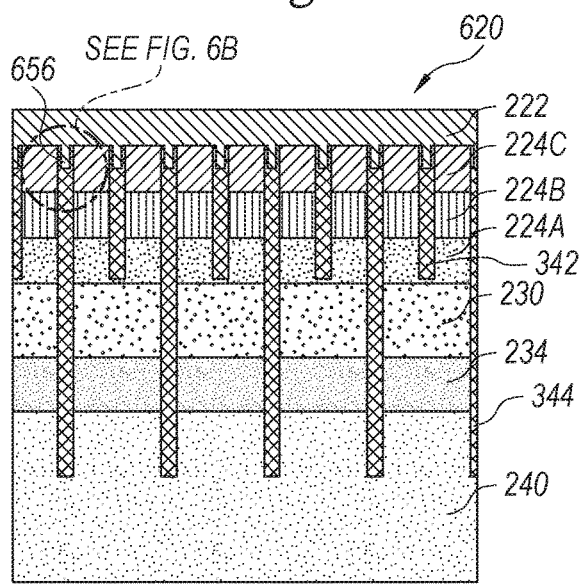
Fig. 6A
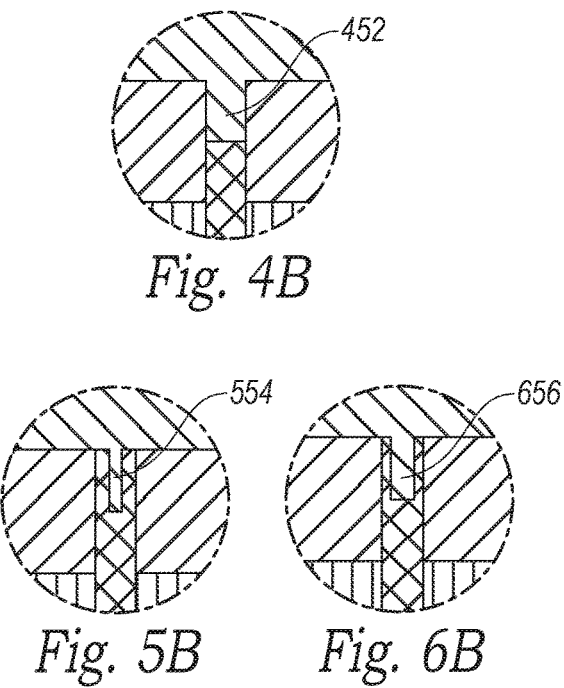
Fig. 4B
Fig. 5B   Fig. 6B

ULTRASOUND TRANSDUCER ASSEMBLY

CROSS-REFERENCE TO RELATED APPLICATIONS

The present application claims priority to U.S. Provisional Application No. 62/214,185, titled ULTRASOUND TRANSDUCER ASSEMBLY, filed on Sep. 3, 2015, which is incorporated herein by reference in its entirety.

TECHNICAL FIELD

The disclosed technology relates generally to ultrasound transducers, and more specifically ultrasound transducer assemblies configured for use with ultrasound imaging systems.

BRIEF DESCRIPTION OF THE DRAWINGS

FIG. 4A is a schematic section view of an ultrasound transducer assembly along the 3-3' line shown in FIG. 1B and configured in accordance with another embodiment of the disclosed technology. FIG. 4B is an enlarged view of a portion of FIG. 4A.

FIG. 5A is a schematic section view of an ultrasound transducer assembly along the 3-3' line shown in FIG. 1B and configured in accordance with another embodiment of the disclosed technology. FIG. 5B is an enlarged view of a portion of FIG. 5A.

FIG. 6A is a schematic section view of an ultrasound transducer assembly along the 3-3' line shown in FIG. 1B and configured in accordance with another embodiment of the disclosed technology. FIG. 6B is an enlarged view of a portion of FIG. 6A.

DETAILED DESCRIPTION

The present technology is generally directed to ultrasound transducer assemblies configured for use with ultrasound imaging systems. In one embodiment, for example.

It will be appreciated that several of the details set forth below are provided to describe the following embodiments in a manner sufficient to enable a person skilled in the relevant art to make and use the disclosed embodiments. Several of the details described below, however, may not be necessary to practice certain embodiments of the technology. Additionally, the technology can include other embodiments that are within the scope of the claims but are not described in detail with reference to FIGS. 1A-8.

Certain details are set forth in the following description and in FIGS. 1A-8 to provide a thorough understanding of various embodiments of the invention. Other details describing well-known methods and systems often associated with ultrasound imaging, however, are not set forth below to avoid unnecessarily obscuring the description of the various embodiments of the invention. Many of the details, dimensions, angles and other features shown in the Figures are merely illustrative of particular embodiments of the disclosure. Accordingly, other embodiments can have other details, dimensions, angles and features without departing from the spirit or scope of the present disclosure. In addition, those of ordinary skill in the art will appreciate that further embodiments of the invention can be practiced without several of the details described below.

In the Figures, identical reference numbers identify identical, or at least generally similar, elements. To facilitate the discussion of any particular element, the most significant digits or digits of any reference number refer to the Figure in which that element is first introduced. For example, element 120 is first introduced and discussed with reference to FIG. 1A.

Figure 1A:
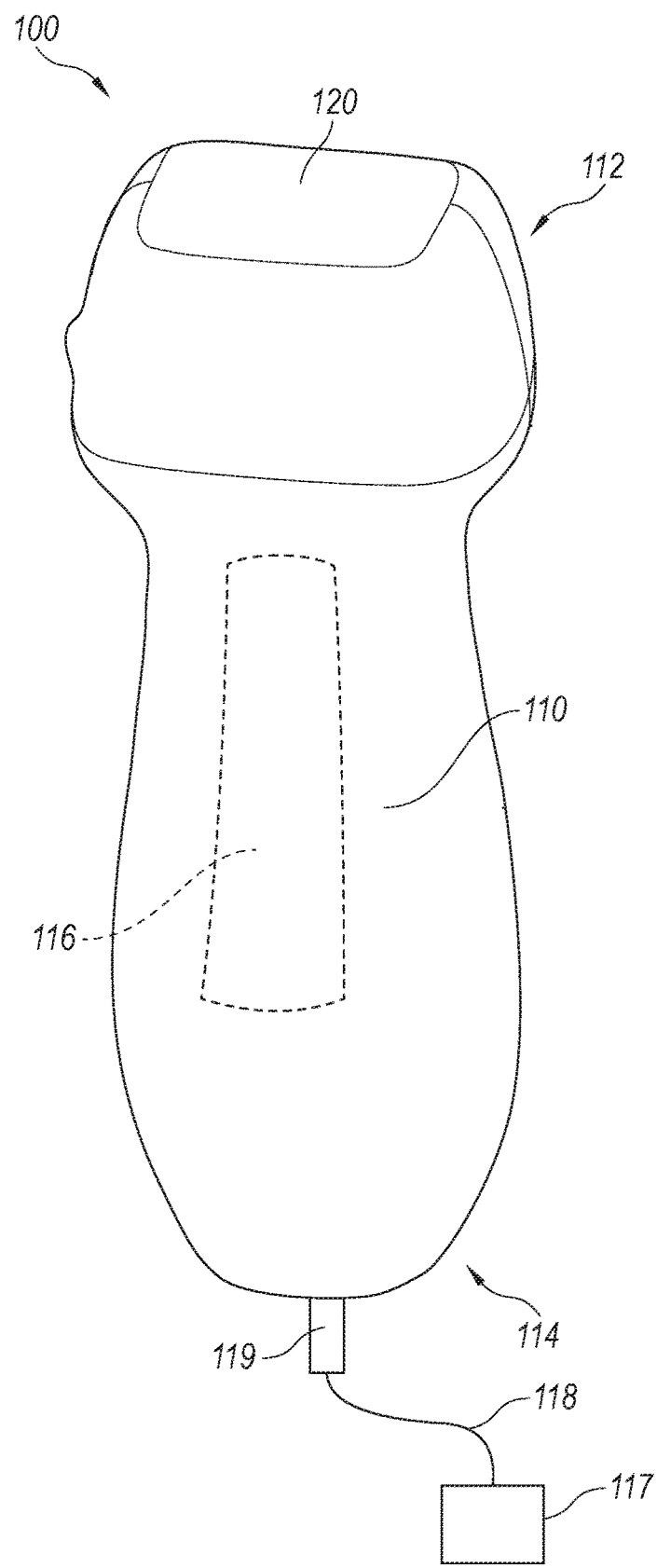
FIG. 1A is a side view of an ultrasound probe having an ultrasound transducer assembly and configured in accordance with an embodiment of the disclosed technology.
Figure 1B:
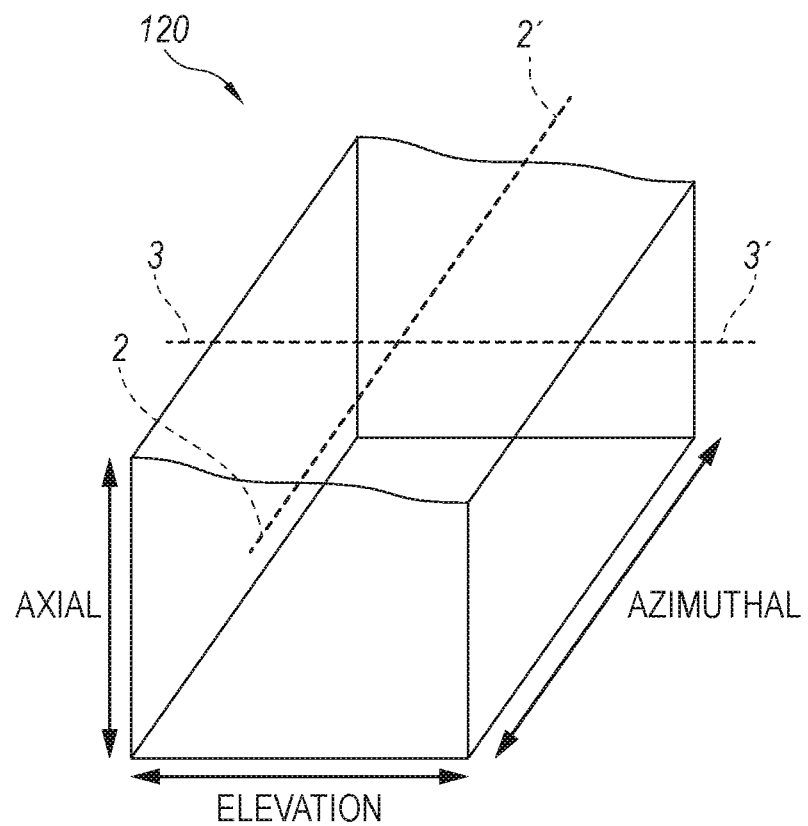
FIG. 1B is a schematic isometric view of a portion of the ultrasound transducer assembly of FIG. 1A.

FIG. 1A is a side view of an ultrasound transducer probe 100 having an ultrasound transducer assembly 120 configured in accordance with an embodiment of the disclosed technology. FIG. 1B is a schematic isometric side view of a portion of the transducer assembly 120 showing the azimuthal (e.g., along an x-axis), elevation (e.g., along a y-axis) and axial (e.g., along a z-axis) dimensions of the transducer assembly 120. Referring now to FIG. 1A, the probe 100 includes an enclosure 110 extending between a distal end portion 112 and a proximal end portion 114. The enclosure 110 is configured to carry or house system electronics 116 (e.g., one or more processors, integrated circuits, ASICs, FPGAs, beamformers, batteries and/or other power sources) disposed in an interior portion or cavity of the enclosure 110. The system electronics 116 are electrically coupled to an ultrasound imaging system 117 via a cable 118 that is attached to the proximal end of the probe by a strain relief element 119. A transducer assembly 120 having one or more transducer elements is electrically coupled to the system electronics 116. In operation, the transducer assembly 120 transmits ultrasound energy from the one or more transducer elements toward a subject and receives ultrasound echoes from the subject. The ultrasound echoes are converted into electrical signals by the one or more transducer elements and electrically transmitted to the system electronics 116 and to electronics (e.g., one or more processors, memory modules, beamformers, FPGAs) in the ultrasound imaging system 117 configured to process the electrical signals and form one or more ultrasound images.

Capturing ultrasound data from a subject using an exemplary transducer assembly (e.g., the transducer assembly 120) generally includes generating ultrasound, transmitting ultrasound into the subject, and receiving ultrasound reflected by the subject. A wide range of frequencies of ultrasound may be used to capture ultrasound data, such as, for example, low frequency ultrasound (e.g., less than 15 MHz) and/or high frequency ultrasound (e.g., greater than or equal to 15 MHz) can be used. Those of ordinary skill in the art can readily determine which frequency range to use based on factors such as, for example, but not limited to, depth of imaging and/or desired resolution.

Figure 2:
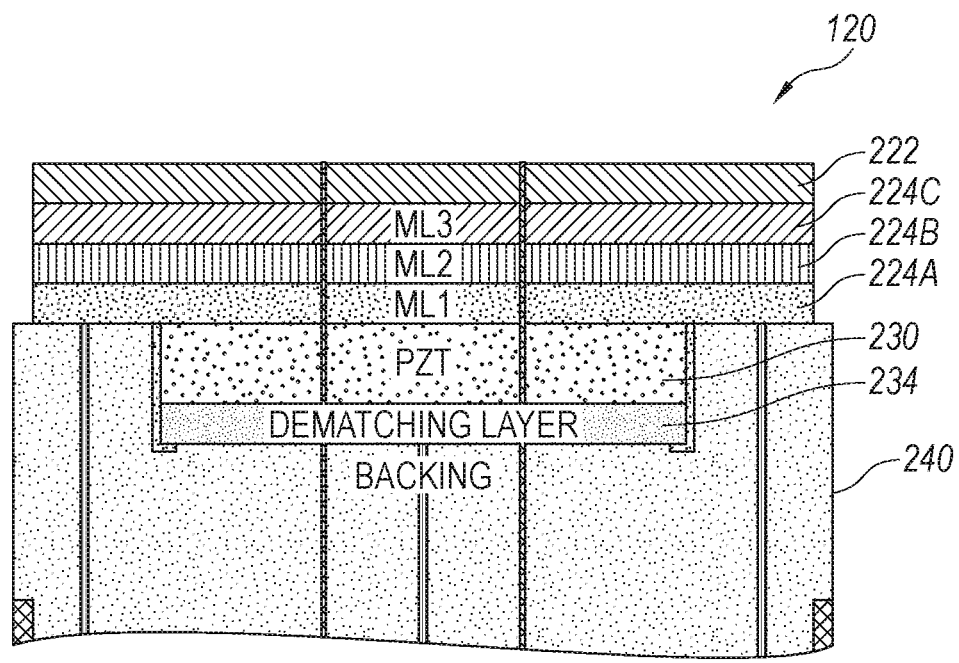
FIG. 2 is a schematic section view of the ultrasound transducer assembly of FIGS. 1A and 1B along the 2-2' line shown in FIG. 1B.

FIG. 2 is a schematic section view of the transducer assembly 120 of FIGS. 1A and 1B shown along the 2-2' line shown in FIG. 1B. A transducer layer 230 includes one or more transducer elements configured to emit ultrasound energy at a center operating frequency (e.g., between 1 MHz and about 10 MHz). In some embodiments, the transducer layer 230 is comprises a piezoelectric material (e.g., lead zirconate titanate, i.e. PZT). In some embodiments, the transducer layer 230 comprises a piezoelectric micromachined ultrasound transducer (PMUT) or a capacitive micromachined ultrasound transducer (CMUT). In some embodiments, the transducer layer 230 comprises an electrostrictive ceramic material. In some embodiments, the transducer layer 230 comprises another suitable transducer material.

An acoustic lens 222 overlies the transducer layer 230 and comprises an acoustically transparent material such as, for example, room temperature vulcanization silicone (RTV) or another suitable acoustic material. A plurality of matching layers 224 is positioned between the lens 222 and the transducer layer 230. A backing layer 240 underlies the transducer layer 230 and is configured to absorb and dissipate acoustic and thermal energy produced by transducer elements of the transducer layer 230. In some embodiments, the backing layer 240 comprises a loaded epoxy (e.g., an epoxy loaded with tungsten particles) and/or another suitable material having one or more plates (not shown) extending therethrough.

A dematching layer 234 is positioned between the transducer layer 230 and the backing layer 240. The dematching layer 234 is configured to reflect rearward propagating ultrasound energy from the transducer layer 230 (i.e., toward the backing layer 240) back toward the front of the transducer assembly 120 (i.e., toward the lens 222) and away from the backing layer 240. In some embodiments, the dematching layer 234 comprises a material that has an acoustic impedance significantly different than an acoustic impedance of the transducer layer 230. In one embodiment, for example, the dematching layer 234 comprises tungsten carbide (WC), which has an acoustic impedance of approximately 100 MRayls-significantly greater than the acoustic impedance of PZT (approximately 34 MRayls).

In other embodiments, however, the dematching layer 234 includes one or more materials having a lower acoustic impedance than the acoustic impedance of WC (e.g., approximately 100 MRayls) and the transducer layer 230. In some embodiments, the dematching layer 234 comprises aluminum nitride (AlN), which has an acoustical impedance of approximately 33 MRayls. In some embodiments, the dematching layer 234 comprises polycrystalline silicon, which has an acoustical impedance of approximately 22 MRayls. In some embodiments, the dematching layer 234 comprises copper loaded graphite having an acoustical impedance between about 8 MRayls and about 15 MRayls, or about 10.7 MRayls. In some embodiments, another suitable dematching layer can be used.

A plurality of matching layers 224 (identified separately as a first matching layer 224A, a second matching layer 224B and a third matching layer 224C) are positioned between the transducer layer 230 and the lens 222. In some embodiments, an acoustical impedance (e.g., between about 20 MRayls and about 35 MRayls) of the transducer layer 230 is greater than an acoustical impedance (e.g., between about 10 MRayls and about 20 MRayls) of the first matching layer 224A. In some embodiments, the acoustic impedance of the first matching layer 224A is greater than an acoustical impedance (e.g., between about 5 MRayls and about 10 MRayls) of the second matching layer 224B. In some embodiments, the acoustical impedance of the second matching layer 224B is greater than an acoustical impedance (between about 2 MRayls and about 5 MRayls) of the third matching layer 224C. Moreover, in the illustrated embodiment of FIG. 2, the transducer assembly 120 includes three matching layers 224. In some embodiments, however, the transducer assembly 120 includes two or fewer matching layers 224. In other embodiments, the transducer assembly 120 includes four or more matching layers 224.

Figure 3:
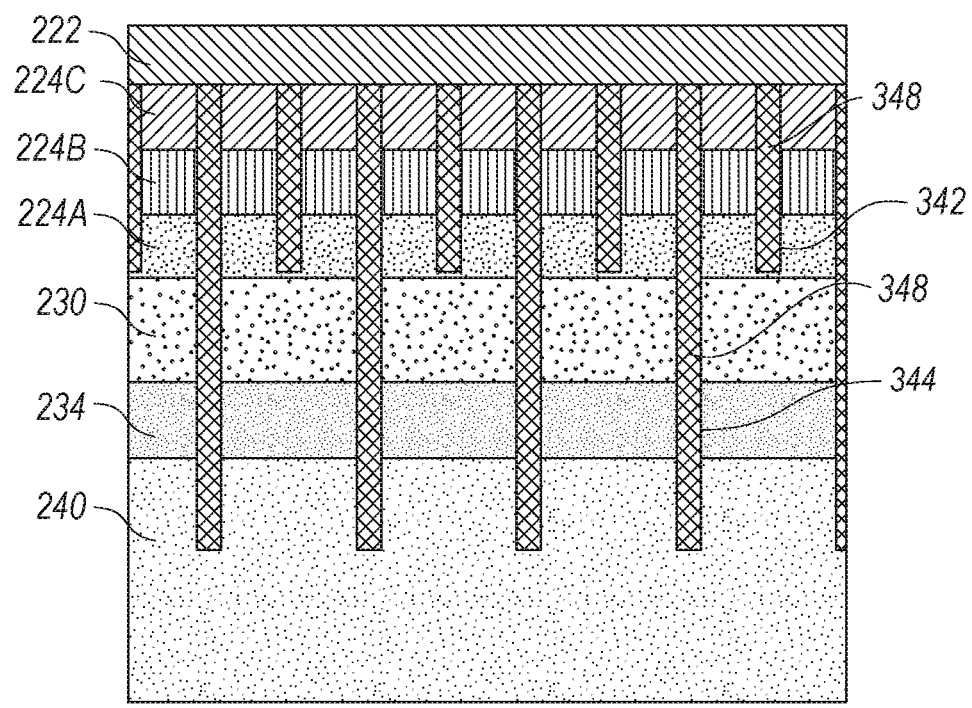
FIG. 3 is a schematic section view of the ultrasound transducer assembly of FIGS. 1A and 1B along the 3-3' line shown in FIG. 1B.

FIG. 3 is a schematic section view of the transducer assembly 120 of FIG. 1B along the 3-3' line shown in FIG. 1B (i.e., parallel to the azimuthal axis), and configured in accordance with various embodiments of the disclosed technology. A plurality of trenches, grooves or first kerfs 342 extend into the transducer assembly 120 a first depth in the axial direction. A plurality of trenches, grooves or second kerfs 344 extend a second depth in the axial direction. In some embodiments, the second depth is greater than the first depth. In other embodiments, however, the first and second depths can be substantially equal. As those of ordinary skill in the art will appreciate, the first kerfs 342 and the second kerfs 344 can be configured to isolate individual elements of the transducer layer 230 and/or attenuate acoustic crosstalk between the individual elements. The first kerfs 342 and the second kerfs 344 are at least partially filled with a filler 348.

In the illustrated embodiment, the first kerfs 342 extend through the matching layers 224 while the second kerfs 344 extend through the matching layers 224, the transducer layer 230 and the dematching layer 234, and extend into the backing layer 240. In other embodiments, however, the first kerfs 342 and the second kerfs 344 can extend to lesser or greater depths relative to the axial direction than shown in FIG. 3. In some embodiments, the first kerfs 342 and the second kerfs 344 have the same depths relative to the axial direction but are filled with different materials. Moreover, In some embodiments, the first kerfs 342 and the second kerf 344 have a same or similar width (e.g., between about 0.01 mm and about 0.1 mm). In other embodiments, however, the first kerfs 342 have a first width that differs from a second width of the second kerfs 344.

The filler 348 comprises one or more materials that fill at least a portion of the first kerfs 342 and the second kerfs 344. In the illustrated embodiment, the depths of the filler 348 in individual first kerfs 342 is substantially the same. Similarly, the depths of the filler 348 in individual second kerfs 344 is also substantially the same. In some embodiments, however, the depths of the filler material 348 in the individual first kerfs 342 and in the individual second kerfs vary in an elevation direction. In some embodiments, for example, an apodized (stepped or curved) depth profile from the edges towards center of the transducer assembly 120 can be utilized. In some embodiments, the first kerfs 342 and the second kerfs 344 are filled with different filler materials.

In some embodiments, the filler 348 comprises a composite material that includes microballoons suspended in an epoxy or a polymer. The microballoons can include glass or plastic microspheres surrounding or encapsulating a gas (e.g., air, or a hydrocarbon gas) or be solid microspheres. The microballoons or microspheres can be mixed with an epoxy or polymer in varying ratios to achieve composite materials having varying consistencies and densities. In some embodiments, for example, a "slurry" composite material is mixed with microballoons and epoxy or a polymer.

In some embodiments, the filler 348 includes a composite material comprising one or more materials, for example, having a density between about 0.0005 g/cm$^3$ and about 0.1 g/cm$^3$ or between about 0.001 g/cm$^3$ and about 0.01 g/cm$^3$ or about 0.0012 g/cm$^3$. In some embodiments, the filler material comprises a composite material having an acoustical impedance within 10% or less of an acoustical impedance of air. In some embodiments, the filler 348 comprises microballoons, an aerogel or a foam. In some embodiments, the filler 348 comprises a composite material that has a graduated acoustical impedance such that the material has an acoustical impedance that varies in the axial direction of the transducer assembly 120. In one embodiment, for example, the graduated acoustical impedance material has an acoustical impedance that decreases with increasing height in the axial direction.

As those of ordinary skill in the art will appreciate, conventional transducer assemblies may include piezoelectric transducers, two matching layers, no dematching layer and kerfs filled with conventional material (e.g., a lens material such as RTV). Such conventional transducer assemblies can have a typical −6 dB bandwidth of 75%. Embodiments of the disclosed technology are expected to provide a benefit of a significant performance increase in bandwidth and efficiency compared to conventional piezoelectric transducer assemblies. Certain embodiments of the disclosed technology, for example, include transducer assemblies that include a −6 dB fractional bandwidth of up to 120% and upto a 8 dB sensitivity gain relative to conventional piezoelectric transducer designs. Embodiments of the disclosed technology are expected to provide an additional benefit of higher mechanical indices (and thus deeper imaging penetration) with lower transmit voltages with similar or identical surface temperatures as conventional piezoelectric transducer assemblies.

FIGS. 4A, 5A, 6A and 7 are schematic section views along the 3-3' line shown in FIG. 1B (i.e., parallel to the azimuthal direction) of transducer assemblies configured in accordance with embodiments of the present disclosure. FIGS. 4B, 5B and 6B are enlarged views of corresponding portions FIGS. 4A, 5A and 6A.

Referring first to FIG. 4, a transducer assembly 420 includes the first kerfs 342 and the second kerfs 344 having a groove 452 formed in the filler 348. The groove 452 has a width in the azimuthal direction substantially similar to widths of the first kerfs 342 and the second kerfs 344. In some embodiments, the first kerfs 342 and the second kerfs 344 can have different groove depths. In the illustrated embodiment of FIGS. 4A and 4B, the groove 452 is filled with the same material (e.g., RTV) as the lens 222. In other embodiments, however, another material may be used.

Referring next to FIG. 5, a transducer assembly 520 includes the first kerfs 342 and the second kerfs having a portion or groove 554 formed in the filler 348. The groove 554 has a smaller width in the azimuthal direction (e.g., ½ as wide, ¼ as wide, ⅛ as wide) than the widths of the first kerfs 342 and the second kerfs 344. In some embodiments, the first kerfs 342 and the second kerfs 344 can have differing groove depths. In the illustrated embodiment of FIGS. 5A and 5B, the groove 554 is filled with the same material (e.g., RTV) as the lens 222. In other embodiments, however, another material may be used.

Referring next to FIG. 6, an ultrasound transducer assembly 620 includes the first kerfs 342 and the second kerfs having a portion or groove 656 formed in the filler 348. The groove 656 has a smaller width in the azimuthal direction (e.g., ½ as wide, ¼ as wide, ⅛ as wide) than the widths of the first kerfs 342 and the second kerfs 344. In some embodiments, the first kerfs 342 and the second kerfs 344 can have differing groove depths. In the illustrated embodiment of FIGS. 5A and 5B, the groove 656 is filled with the same material (e.g., RTV) as the lens 222. In other embodiments, however, another material may be used.

Figure 7:
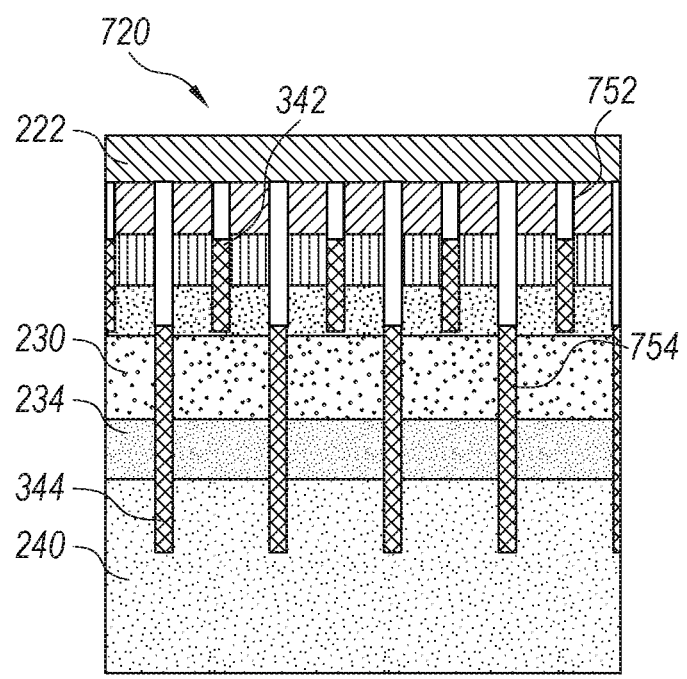
FIG. 7 is a schematic section view of an ultrasound transducer assembly along the 3-3' line shown in FIG. 1B and configured in accordance with another embodiment of the disclosed technology.

Referring now to FIG. 7, an ultrasound transducer assembly 720 includes the first kerfs 342 and the second kerfs having a first filler material 752 (e.g., a polymer) above a second filler material 754 (e.g., a composite material comprising microballoons). In some embodiments, grooves can be formed in the first filler material 752 as described above in reference to FIGS. 4A-6B.

Figure 8:
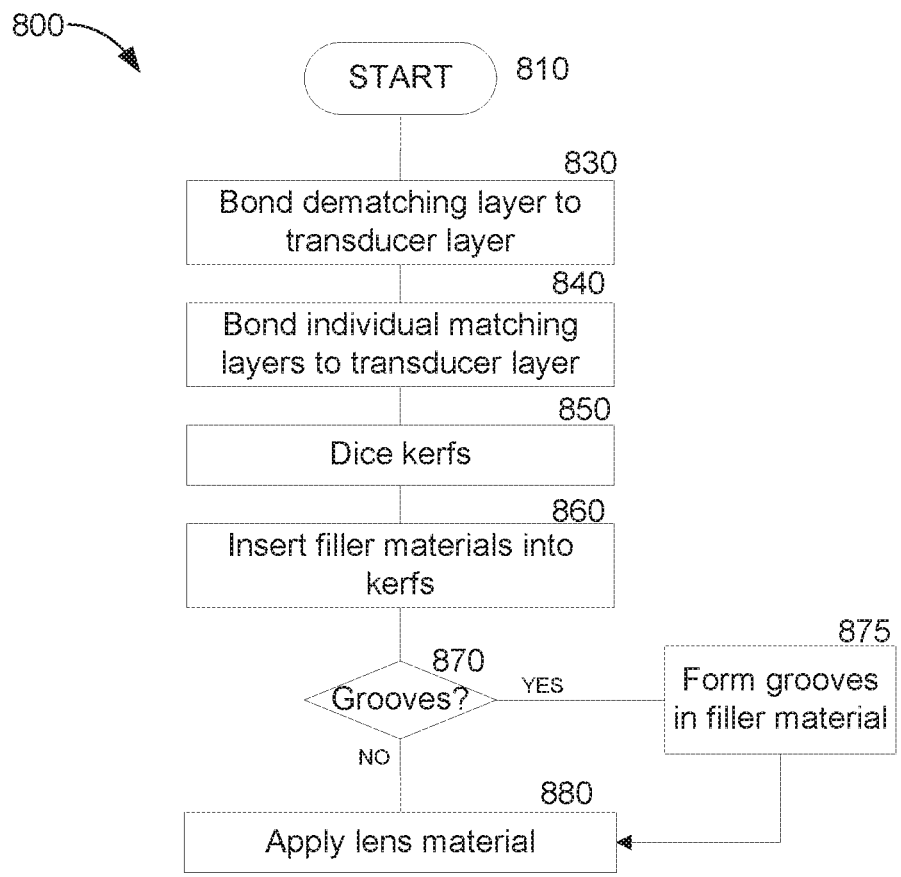
FIG. 8 is a flow diagram of a method of constructing an ultrasound transducer assembly configured in accordance with an embodiment of the disclosed technology.

FIG. 8 is a flow diagram of a process 800 of constructing an ultrasound transducer assembly in accordance with an embodiment of the disclosed technology. At block 810, the process 800 begins. At block 830, the process 800 bonds a lower surface of a transducer layer (e.g., the transducer layer 230 of FIG. 2) to an upper surface of the dematching layer using an adhesive (e.g., an epoxy, a polymer). At block 840, the process 800 bonds a first matching layer to the transducer layer and bonds one or more additional matching layer to the first matching layer. In some embodiments, the process 800 can optionally bond a lower surface of a dematching layer (e.g., the dematching layer 234 of FIG. 2) to an upper surface of a backing layer (e.g., the backing layer 240 of FIG. 2) using an epoxy. At block 850, the process 800 performs one or more cuts to form one or more kerfs (e.g., the first kerfs 342 or the second kerfs 344 of FIG. 3) in the transducer assembly. At block 860, the process 800 inserts or otherwise fills at least a portion of the kerfs formed at block 850 with a filler material (e.g., a filler material comprising microballoons).

At decision block 870, the process 800 determines whether one or more grooves is to be formed in the filler material inserted into the kerfs formed at block 860. If so, then the process 800 proceeds to block 875 and one or more kerfs are formed in the filler material inserted into the kerfs at block 860 (e.g., the grooves 452 of FIGS. 4A and 4B, the grooves 554 of FIGS. 5A and 5B and/or the grooves 656 of FIGS. 6A and 6B). At block 880, a lens material (e.g., RTV or another suitable lens material) is applied onto the front (i.e., on the uppermost matching layer) of the transducer assembly.

Unless the context clearly requires otherwise, throughout the description and the claims, the words "comprise," "comprising," and the like are to be construed in an inclusive sense, as opposed to an exclusive or exhaustive sense; that is to say, in the sense of "including, but not limited to." As used herein, the terms "connected," "coupled," or any variant thereof means any connection or coupling, either direct or indirect, between two or more elements; the coupling or connection between the elements can be physical, logical, or a combination thereof. Additionally, the words "herein," "above," "below," and words of similar import, when used in this application, refer to this application as a whole and not to any particular portions of this application. Where the context permits, words in the above Detailed Description using the singular or plural number may also include the plural or singular number respectively. The word "or," in reference to a list of two or more items, covers all of the following interpretations of the word: any of the items in the list, all of the items in the list, and any combination of the items in the list.

The above Detailed Description of examples of the disclosed technology is not intended to be exhaustive or to limit the disclosed technology to the precise form disclosed above. While specific examples for the disclosed technology are described above for illustrative purposes, various equivalent modifications are possible within the scope of the disclosed technology, as those skilled in the relevant art will recognize.

The teachings of the disclosed technology provided herein can be applied to other systems, not necessarily the system described above. The elements and acts of the various examples described above can be combined to provide further implementations of the disclosed technology. Some alternative implementations of the disclosed technology may include not only additional elements to those implementations noted above, but also may include fewer elements. For example, in some implementations, transducer assemblies configured in accordance with the disclosed technology may include fewer than three matching layers or four or more matching layers. In other implementations, transducer assemblies can be configured in accordance with the disclosed technology without a dematching layer.

These and other changes can be made to the disclosed technology in light of the above Detailed Description. While the above description describes certain examples of the disclosed technology, and describes the best mode contemplated, no matter how detailed the above appears in text, the disclosed technology can be practiced in many ways. Details of the system may vary considerably in its specific implementation, while still being encompassed by the disclosed technology disclosed herein. As noted above, particular terminology used when describing certain features or aspects of the disclosed technology should not be taken to imply that the terminology is being redefined herein to be restricted to any specific characteristics, features, or aspects of the disclosed technology with which that terminology is associated. In general, the terms used in the following claims should not be construed to limit the disclosed technology to the specific examples disclosed in the specification, unless the above Detailed Description section explicitly defines such terms.

We claim:

1. An ultrasound transducer assembly comprising:
a transducer layer configured emit ultrasound energy in an axial direction;
a plurality of matching layers overlaying the transducer layer in the axial direction; a lens over the plurality of matching layers; and
a plurality of kerfs extending from the lens into the plurality of matching layers, wherein each kerf of the plurality of kerfs is at least partially filled with a first filler material comprising microballoons or microspheres and contains a groove in the first filler material in said each kerf at a portion of the plurality of matching layers adjacent to the lens, the groove having a width less than a width of said each kerf in which the groove is contained and is filled with a second filler material different than the first filler material.

2. The ultrasound transducer assembly of claim 1 wherein the plurality of kerfs include a plurality of first kerfs and a plurality of second kerfs, wherein the first kerfs have a first depth in the axial direction, wherein the second kerfs have a second depth in the axial direction greater than the first depth.

3. The ultrasound transducer assembly of claim 2, further comprising a backing layer underlying the transducer layer.

4. The ultrasound transducer assembly of claim 2, further comprising a dematching layer between the transducer layer and the backing layer, wherein the second kerfs extend into the backing layer through the plurality of matching layers, the transducer layer and the dematching layer.

5. The ultrasound transducer assembly of claim 4 wherein the acoustical impedance of the dematching layer is less than the acoustical impedance of tungsten carbide.

6. The ultrasound transducer assembly of claim 1, wherein the kerfs have a first width in an azimuthal direction, and wherein the groove has a second width in the azimuthal direction less than the firstwidth.

7. The ultrasound transducer assembly of claim 6 wherein the second width is greater than one half of the first width.

8. The ultrasound transducer assembly of claim 6 wherein the second width is less than one quarter of the first width.

9. The ultrasound transducer assembly of claim 6 wherein the groove has a depth in the axial direction less than a thickness of the matching layer.

10. The ultrasound transducer assembly of claim 6 wherein the groove has a depth in the axial direction greater than a thickness of the matching layer.

11. The ultrasound transducer assembly of claim 1 wherein the depths of the first filler material in individual kerfs in an axial direction varies in an azimuthal direction.

12. The ultrasound transducer assembly of claim 1 wherein the depths of the first filler material in individual kerfs in an axial direction varies in an elevation direction.

13. The ultrasound transducer assembly of claim 1 wherein the first filler material includes an acoustical impedance that is graduated in an axial direction.

* * * * *